United States Patent [19]

Gros

[11] Patent Number: 4,626,433
[45] Date of Patent: Dec. 2, 1986

[54] REMEDY FOR HEMORRHOIDS

[75] Inventor: Chester P. Gros, New Orleans, La.

[73] Assignee: Preparation Gold, Inc., New Orleans, La.

[21] Appl. No.: 735,599

[22] Filed: May 20, 1985

[51] Int. Cl.$^4$ .............................................. A61K 33/06
[52] U.S. Cl. .................................. 424/154; 514/882; 514/966
[58] Field of Search ................ 514/882, 966; 424/154

[56] References Cited

PUBLICATIONS

Handbook of Non Prescription Drugs, 5th ed., 1977, pp. 63–69.
Merck Index, 9th ed., 1976, p. 49.

Primary Examiner—Leonard Schenkman
Attorney, Agent, or Firm—Pravel, Gambrell, Hewitt & Kimball

[57] ABSTRACT

A hemorrhoidal remedy which comprises a salve consisting primarily of aluminum potassium sulfate, linseed oil, methanol, camphor and pure petroleum jelly. There is further provided a process for combining the aluminum potassium sulfate and mixing thoroughly with one ounce of linseed oil. Upon the aluminum sulfate and the linseed oil being thoroughly mixed, there is then added approximately one-half ounce of menthol, one quarter ounce of camphor to the mixture of the aluminum potassium sulfate and linseed oil. Following the thorough mixing of these ingredients, the pure petroleum jelly is added in and thoroughly mixed, utilizing approximately four ounces of the jelly.

4 Claims, No Drawings

REMEDY FOR HEMORRHOIDS

BACKGROUND OF THE PRESENT INVENTION

1. Technical Field

The present invention relates to treatment of hemorrhoids. More particularly, the present invention relates to an ointment for treating hemorrhoids and the application of the treatment for remedying the condition.

2. General Background

Hemorrhoids, or piles as they are commonly known, are an anal rectal condition which have been the subject of numerous types of treatment for remedying the discomfort associated with them. There have been many historically many possible causes cited of hemorrhoids including hormones, genes, inflammation and/or infection, constipation, exercise, diet, laxation, amongst others. Although hemorrhoids are not considered as serious as other rectal diseases, the high incidence of hemorrhoids in age groups between 20 and 50 has attributed to a desire to find a suitable remedy for them.

Medically, hemorrhoids are anorectal swellings, composed of varicosities involving one or more of the hemorrhoidal plexus of veins. Pathologically, the process is a degeneration of the hemorrhoidal plexus, including dilation of the veins and thinning of their walls, resulting in complications such as inflammation, edema, ulceration and thrombosis. The process is characterized by bleeding and protrusions which occur in the lowest portion of the rectum, in the anal canal or at the anal margin.

Most treatment of hemorrhoids is combined to cases where the symptoms would hinder normal activity. The general therapy presently in the art for treating hemorrhoids is medical, surgical or injectional. The treatment overall is for symptoms only, and it is mainly to reduce pain, itching and inflammation and bleeding and to prevent further complications.

There are more than two hundred ointments and suppository products utilized in the treatment of hemorrhoids. Hemorrhoids is one of the most frequently self-treated conditions affecting people, and due to the fear and embarassment with having them treated, patients frequently self-medicate, with many over the counter treatment remedies.

Of the type of remedies that are presently on the market, combinations of traditional ingredients such as local anesthetics, vasoconstrictors, antiseptics, and mild astringents. Other ingredients used in the over the counter hemorrhoidal preparations include those intended to promote skin healing. However, the affects of the these particular products has not met with great success.

The following patents have been obtained which make reference to treatment of hemorrhoids as they are commonly known:

U.S. Pat. No. 3,415,249; issued to Sperti and entitled "Suppository" discloses a suppository having a first and second body wherein the first body is a suppository base and the second body consists essentially of a vehicle and an anesthetic. The two bodies are joined at a common surface such that the second body being of such character as to become liquified when inserted.

U.S. Pat. No. 3,262,849, issued to Lietz, et al. entitled "Suppository Base Compositions," relates to a base material for suppository which would contain a pharmaceutically active ingredient wherein the base material would comprise a condensation of high molecular fatty alcohols, and mixed with alkali methal and alkaline earth metal soaps to provide a base material for suppositories which has a short solidification period enabling it to harden rapidly without special cooling means.

U.S. Pat. No. 2,241,331, issued to Shelton and entitled "Suppository," relates to an improved suppository wherein the base includes a principal ingredient, an ester of a polyhydric alcohol having four to six hydroxyl groups or an anhydride, particularly an ester of a sugar alcohol or a mixture of such esters.

U.S. Pat. No. 1,890,596, issued to Zographos and entitled "Remedy For Hemorrhoids," relates to a salve or ointment for a remedy for hemorrhoids which is applied locally to the affected parts, the remedy consisting primarily of mutton tallow, pure glycerine, powdered calomel and green and tansy weed.

U.S. Pat. No. 979,395, issued to Straub entitled "Pile Remedy," discloses a composition for treating hemorrhoids which comprises primarily of caraway leaves, water, gylcerine, and vaseline wherein beeswax can also be included.

U.S. Pat. No. 950,658, issued to Cadenhead entitled "Opium Ointment," relates to an improved composition of making a salve for use in the treatment of piles which consists of finely divided pine cone ashes, powder opium and petroleum and a method of combining same.

U.S. Pat. No. 147,898, issued to Cannon entitled "Improvement In Medical Compounds Or Ointments," pertains to salve for piles which is composed of hog's lard and hog's hair flavored with the essence of cinnamon or other flavoring substances.

In addition, applicant has cited as prior art an article entitled "Hemorrhoidal Products" by Dr. K. Richard Knoll which makes reference to, on pages 67-69, the various hemorrhoidal products currently on the market and available.

SUMMARY OF THE PRESENT INVENTION

The treatment remedy of the present invention relates to a hemorrhoidal treatment which comprises a salve consisting primarily of aluminum potassium sulfate, raw or boiled linseed oil, natural menthol, camphor and pure petroleum jelly. There is further provided a process for combining the various constituents on a percentage basis by weight. For example, by weight, the aluminum potassium sulfate would be mixed thoroughly with one ounce of linseed oil. Upon the aluminum sulfate and the linseed oil being thoroughly mixed, there is then added approximately onehalf ounce of menthol, one quarter ounce of camphor to the mixture of the aluminum potassium sulfate and linseed oil. Following the thorough mixing of these ingredients, the pure petroleum jelly is added in and thoroughly mixed, utilizing approximately four ounces of the jelly. The preferable permissable percentages for each component in a given mix are as follows:

Aluminum Potassium Sulfide: 1%-27%
Linseed Oil: 1%-24%
Natural Menthal: 1%-19%
Camphor Oil: 1%-18%
Petroleum Jelly (Carrier): 12%-96%

Based on percentages, however, the mixture would preferably include 17% aluminum potassium sulfate, 14% linseed oil, 8% camphor oil, 9% natural menthol and 52% pure petroleum jelly as a carrier. Although not being bound by theory, the aluminum potassium sulfate when mixed with the linseed oil are the two primary ingredients that causes the constriction and drying of hemorrhoids. The aluminum potassium sulfate serves as an astringent on the hemorrhoids while the linseed oil when exposed to oxygen tends to dry the hemorrhoids. The menthol and camphor acts as the antiseptics and coacts with the aluminum potassium sulfate and linseed oil. The pure petroleum jelly forms the remainder of the body of the salve and also serves as an oil that keeps the inner orifice and canal lubricated.

Therefore, the principal object of the present invention relates a remedy for stopping the bleeding, pain and itching in external and internal hemorrhoidal conditions.

It is still a further principal object of the present invention to provide a mixture of ingredients for applying to hemorrhoids to effect drying and constriction of the hemorrhoids following application.

DETAILED DESCRIPTION OF THE PREFERRED EMBODIMENT

The preferred embodiment of the present invention shall be first discussed in terms of the ingredients involved in the hemorrhoidal remedy of the present invention. Secondly, the embodiment will discuss the overall action of the ingredients during the treating process. In the preparation of the present invention, the following steps are taken to be the preferred embodiment. Initially, there are provided the ingredients of aluminum potassium sulfate and a quantity of linseed oil, these two first primay ingredients being the two key ingredients which causes the hemorrhoids to constrict and dry. There is further provided a quantity of menthol and camphor which serve as the antiseptic for coacting the aluminum potassium sulfate and linseed oil in the drying and constricting process. The final ingredient would comprise pure petroleum jelly for forming the remainder of the body of the ointment for acting as a lubricant for the anal orifice and canal.

In the preferred embodiment, by weight of ingredients, one ounce of the aluminum potassium sulfate is mixed thoroughly with one ounce of linseed oil, as a normal treatment base. Following the thorough mixing of these two ingredients, there is then mixed into the mixture a one-half ounce of menthol and a one-quarter ounce of camphor. These four ingredients are then mixed very thoroughly. Upon completion of the mixture of the four ingredients, the final ingredient, pure petroleum jelly, is thoroughly mixed in, using four ounces of jelly. Therefore, upon completion of the mixture, one would have approximately seven ounces of the ointment in its thoroughly mixed state for application.

In the preferred embodiment, the combination of ingredients on a percentage basis would be 17% of aluminum potassium sulfate is mixed thoroughly with 14% linseed oil, as a normal treatment base. Following the thorough mixing of these two ingredients, there is then mixed into the mixture 2% menthol and 8% camphor. These four ingredients are then mixed very thoroughly. Upon completion of the mixture of the four ingredients, the final ingredient, pure petroleum jelly, is thoroughly mixed in, using 52% jelly.

As was stated earlier, the aluminum potassium sulfate when mixed with the linseed oil are the principal ingredients for causing the hemorrhoids to constrict and dry. Actually, the aluminum potassium sulfate serves as the astringent on the hemorrhoids while the linseed oil, when exposed to oxygen, tends to dry the infected area. The menthol and camphor serves as the antiseptic coacting the aluminum potassium sulfate and linseed oil.

The application of the particular ointment is the normal application as with other remedies and it is the overall combination of these ingredients that form the application of the present invention.

Because many varying and different embodiments may be made within the scope of the inventive concept herein taught, and because many modifications may be made in the embodiment of the law, it is to be understood that the details herein are to be interpreted as illustrative and not in a limiting sense.

What is claimed as invention is:

1. A composition for topically treating hemorrhoids, which comprises:
   a. a lubricating base containing a mixture of; aluminum potassium sulfate, linseed oil, menthol, and camphor.

2. The composition of claim 1, wherein the ratio of aluminum potassium sulfate and linseed oil is approximately a 50:50 ratio by weight.

3. The composition of claim 1, wherein the ratio of menthol and camphor is approximately a 4:1 ratio of menthol to camphor by weight.

4. The composition of claim 1, wherein the composition comprises percentage by weight of aluminum potassium sulfate—17%; linseed oil—14%; menthol—9%; camphor—8%; and lubricating base—52%.

* * * * *